United States Patent
Sponsel et al.

[11] Patent Number: 6,046,223
[45] Date of Patent: Apr. 4, 2000

[54] TREATMENT OF MACULAR EDEMA

[75] Inventors: William Eric Sponsel, San Antonio, Tex.; Alon Harris, Indianapolis, Ind.

[73] Assignee: Advanced Research & Technology Institute, Indianapolis, Ind.

[21] Appl. No.: 08/806,866

[22] Filed: Feb. 25, 1997

Related U.S. Application Data

[60] Provisional application No. 60/012,250, Feb. 26, 1996.

[51] Int. Cl.$^7$ ................................................ A61K 31/425
[52] U.S. Cl. .......................................... 514/372; 514/912
[58] Field of Search ..................................... 514/372, 912

[56] References Cited

FOREIGN PATENT DOCUMENTS 2 203 039  10/1988  United Kingdom .
WO 94/15582  7/1994  WIPO .

OTHER PUBLICATIONS

Wilkerson et al.—Arch Ophthalmol/vol. 11, Oct. 1993—Four–week Safety and Efficacy Study of Dorzolamide, a Novel, Active Topical Carbonic Anhydrase Inhibitor.
Y. Kitazawa et al.—Journal of Glaucoma 3275–279—Dorzolamide, A topical Carbonic Anhydrase Inhibitor: A Two–Week Dose–Response Study in Patients with Glaucoma or Ocular Hypertension.
J. Messerli—Schweiz Med. Wochenschr., Vo. 123, No. 16, 1993, pp. 783–788—Akuter Visusverlust infolge okularer Durchblutungsstorunge.
Ghiou et al.—Journal of Ocular Pharmacology—vol. 9, No. 1, 1993—Effects of Antiglaucoma Drugs on Ocular Blood Flow in Ocular Hypertensive Rabbits.
Rassam et al.—Eye (1993) 7,697–702—The Effect of Acetazolamide on the Retinal Circulation.
Farber et al.—Reduction of macular oedema by acetazolamide in patients with chronic iridocyclitis: a randomised prospective crossover study—British Journal of Ophthalmology 1994; 78: 4–7.
Fishman et al.—Rebound of Macular Edema With Continue Use of Methazolamide in Patients with Retinitis Pigmentosa111, Dec. 1993, p. 1640–1646.
E–Mail from Amon to Oschmann—dated Jan. 15, 1996.
E–Mail from Amon to Korsen—dated Jan. 18, 1996.
E–Mail from Korsen to Amon—dated Jan. 18, 1996.
E–Mail from Amon to Korsen—dated Jan. 18, 1996.
E–Mail from Amon to Daniel and Korsen—dated Jan. 22, 1996.
E–Mail from Treloar to Ammon—dated Feb. 5, 1996.
E–Mail from Amon to Botelho—dated Feb. 5, 1996.
Statement of Amon accompanying Complaint filed by Sponsel against Merck—dated Feb. 10, 1997.
Statement of Vogel accompanying Complaint filed by Sponsel against Merck—dated Feb. 10, 1997.

*Primary Examiner*—Zohreh Fay
*Attorney, Agent, or Firm*—McDermott, Will & Emery

[57] ABSTRACT

There is disclosed a method for treating and/or preventing macular edema and age-related macular degeneration which comprises topical administration of carbonic anhydrase inhibitors to the eye.

30 Claims, No Drawings

TREATMENT OF MACULAR EDEMA

This application claims priority from Provisional United States Application Serial No. 60/012,250, filed Feb. 26, 1996.

BACKGROUND OF THE INVENTION

Macular edema is swelling within the retina within the critically important central visual zone at the posterior pole of the eye. An accumulation of fluid within the retina tends to distract the neural elements from one another and from their local blood supply, creating a dormancy of visual function in the area. Usually the process is self-limiting, but permanent visual disability occasionally results. Often times, the swelling may take many months to clear. The precise mechanism by which swelling is triggered is uncertain, but it is probable that certain natural metabolic toxins may play an important role in the disease process. Swelling may also follow the implantation of plastic lenses after cataract surgery, particularly if there is a breech in the lens capsule which segregates the vitreous gel from the fluid filled anterior chamber. Long standing macular edema after cataract surgery is one of the most frustrating situations in all of opthamology, and is remarkably common.

It was first reported by Cox et al, Arch. Ophthalmol., Vol. 106, Sept. 1988, pp. 1190–95, that oral acetazolamide (DIAMOX®) can cause resolution of chronic macular edema of various causes. In this study, 16 of 41 patients showed a reproducible response to the drug with partial or complete resolution of edema and improvement of visual acuity. The therapeutic effect occurred in more than half of the patients with inherited outer retinal disease or uveitis, but in none with primary retinal vascular disorders. Additional studies have corroborated Cox's findings with acetazolamide (Fishman et al., Arch. Ophthalmol. 1989; 107:1445–1452 and Chen et al., Invest. Ophthalmol. Vis. Sci. 1991; 31:1914–1918) and others have utilized the carbonic anhydrase inhibitor methazolamide (Fishman et al., Arch. Ophthalmol. 1993; 111:1640–1646).

Studies of patients who have proven to be responsive to acetazolamide treatment typically show pigment epithelial cell dysfunction. These cells, which line the innermost layer of the choroid, have villi-like projections which interdigitate with the retinal photoreceptors. This flexible but intimate association between pigment epithelial cells and photoreceptors is of critical importance to retinal health. The photoreceptors are highly active metabolically and produce waste products at a great rate. The pigment epithelial villi typically absorb catabolites, regenerate photo pigment and provide nutrients via their closely associated choriocapillaris vascular network. Fluorescein angiography of the pigment epithelium in individuals with macular edema who have shown to be responsive to acetazolamide demonstrate leakage of dye into the photoreceptor area. This leakage is inhibited by treatment with acetazolamide.

There are a number of theories as to how carbonic anhydrase inhibitors (CAIs) might work on macular edema however none have been conclusively detemined. At least 14 different etiologic subtypes of macular edema exist, and it is probable that some will prove to be more responsive to topical CAI treatment than other types. Some of the above-mentioned studies lay a basis for this.

Another even more common chronic condition which has typically been presumed to be irreversible is macular degeneration. Macular degeneration is the most common cause of acquired legal blindness. Instead of fluid accumulating in the outer retina, hard accumulations of lipofuscin, a metabolic waste product, tend to accumulate between the photoreceptors and the villi of the retina pigment epithelium. These accumulations gradually enlarge, and in their early pathologic phase create discrete accumulations known as drusen. The lipofuscin is belived to accumulate as a result of a process known as apoptosis, a breaking off of the photoreceptor elements. Shedding of the cellular components of the photoreceptors is constantly occurring in a healthy retina. Good retinal pigment epithelial metabolism generally insures a rapid clearance of such catabolic byproducts of vision. It is interesting to consider that an improved local circulation or a stabilization of membrane pH gradience might retard or prevent the accumulation of lipofuscin. As drusen accumulate in number and begin to coalesce, vast areas of retinal photoreceptors become permanently disengaged from their neighboring retinal pigment epithelial villi. The sections of retina so effected become blind. The greatest propensity among the aging population is for drusen to accumulate in the very central area of vision, the macula. Current therapy lacks any substantive clinical scientific basis with zinc in tablet form as one attempted method of treatment. Thus, a method of treating and/or preventing age-related macular degeneration would be welcomed by the medical community.

SUMMARY OF THE INVENTION

It has now been found that drugs in the class of carbonic anhydrase inhibitors (CAIs) when administered topically are useful in the treatment and/or preventing of macular edema and Age-Related Macular Degeneration (ARMD). CAIs include such drugs as dorzolamide, acetazolamide, methazolamide and other compounds which are described in U.S. Pat. Nos. 5,153,192, 5,300,499, 4,797,413, 4,386,098, 4,416,890 and 4,426,388; and in pending patent application 93/16701. The disclosures of the above US patents and patent applications are hereby incorporated by reference. The compounds disclosed in these applications, if able to be formulated as a topical agent, would be considered to be effective in the treatment discussed herein. Dorzolamide, S,S-5,6-dihydro-4-ethylamino-6-methyl-4H-thieno-[2,3-b] thiopyran-2-sulfonaimide-7,7 dioxide hydrochloride and its trans enantiomer are useful in the treatment of ocular hypertension associated with glaucoma. CAIs manifest their activity by inhibiting the enzyme, carbonic anhydrase, and impeding their contribution to aqueous humour formation made by the carbonic anhydrase pathway. CAIs block or impede this inflow pathway by inhibiting carbonic anhydrase. Dorzolamide, which is also known under its trademark, TRUSOPT®, is the first topically effective CAI for clinical use.

DETAILED DESCRIPTION OF THE INVENTION

The present invention is directed to a method of treating and/or preventing macular edema by topical application of CAIs to the eye. The present invention is also directed to a method of treating and/or preventing macular degeneration by topical application of CAIs to the eye. In particular, it has been found that Dorzolamide can effectively improve the vision of patients suffering from macular edema.

In particular, the method of treating and/or preventing macular edema and macular degeneration comprises topically administering a compound having the formula:

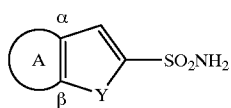
(I)

wherein A together with the two carbon atoms denoted as α and β is the group

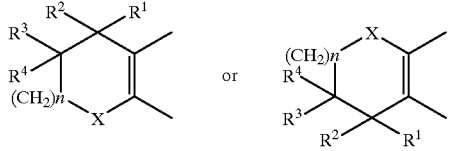

wherein:
X is —S—, —SO—, —SO$_2$— or —CH$_2$—;
Y is —S—, —O—, or —NR$^3$— wherein R$^3$ is hydrogen, C$_{1-3}$alkyl, or benzyl;
n is 1 or 2;
R$^1$, R$^2$, R$^3$, R$^4$ are independently selected from:
1) hydrogen,
2) OR$^5$ wherein R$^5$ is:
  a) hydrogen,
  b) C$_{1-5}$ alkyl, either unsubstituted or substituted with —OH, or

wherein R$^6$ and R$^7$ are independently hydrogen or C$_{1-5}$ alkyl, or joined together form a heterocycle with the nitrogen to which they are attached such as piperidino, morpholino, or piperazino,
  c) C$_{1-5}$ alkanoyl, either unsubstituted or substituted with —OH, —NR$^6$R$^7$, —NH—COR$^8$ or —COR$^8$ wherein R$^8$ is —OH, —NR$^6$R$^7$ or C$_{1-5}$ alkoxy,
  d) —CO—R$^9$, wherein R$^9$ is —NR$^6$R$^7$ or a 5- or 6-membered aromatic heterocycle such as pyridyl, imidazolyl, pyrazinyl, thiazolyl, thienyl, or oxazolyl,
3) —NR$^6$R$^7$,
4) —NHR$^{10}$ wherein R$^{10}$ is:
  a) —SO$_2$NR$^6$R$^7$,
  b) —SO$_2$R$^{11}$, wherein R$^{11}$ is C$_{1-5}$ alkyl, or
  c) —CONR$^6$R$^7$,
5) C$_{1-5}$ alkyl, either unsubstituted or substituted with
  a) —OR$^5$,
  b) —CN,
  c) —NR$^6$R$^7$, or
  d) —COR$^8$,
6) —SO$_2$R$^{11}$,
7) —SO$_2$NR$^6$R$^7$, or
8) -halo, such as chloro, bromo or fluoro;
R$^1$ and R$^3$, or R$^2$ and R$^4$ taken together represent a double bond;
R$^1$ and R$^2$, or R$^3$ and R$^4$ taken together represent
1) =O, or
2) =NOR$^{12}$ wherein R$^{12}$ is hydrogen or C$_{1-3}$alkyl; and one of the —CH$_2$— groups of —(CH$_2$)$_n$— can be substituted with —COR$^8$, —CH$_2$R$^8$, or —CH$_2$COR$^8$.

The compounds of formula I are described in and prepared by methods set forth in U.S. Pat. No. 4,797,413, the disclosure of which is hereby incorporated by reference.

Additionally, the method comprises topically administering a thiophene sulfonamide compound having the formula:

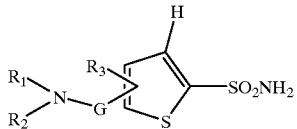
(II)

or a pharmaceutically acceptable salt thereof wherein;
R$_1$ is H; C$_{1-4}$ alkyl; C$_{2-4}$ alkyl substdtuted optionally with OH, halogen, C$_{1-4}$ alkoxy or C(=O)R$_7$.
R$_2$ is H; C$_{1-8}$ alkyl; C$_{2-8}$ alkyl substituted with OH, NR$_5$R$_6$, halogen, C$_{1-4}$ alkoxy or C(=O)R$_7$; C$_{3-7}$ alkenyl unsubstituted or substituted optionally with OH, NR$_5$R$_6$, or C$_{1-4}$ alkoxy; C$_{3-7}$ alkynyl unsubstituted or substituted optionally with OH, NR$_5$R$_6$, or C$_{1-4}$ alkoxy; C$_{1-3}$ alkyl substituted with phenyl or heteroaryl which can be unsubstituted or substituted optionally with OH, C(H$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2; C$_{2-4}$ alkoxy substituted optionally with NR$_5$R$_6$, halogen, C$_{1-4}$ alkoxy, or C(=O)R$_7$; phenyl, or heteroaryl, unsubstituted or substituted optionally with OH, (CH$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2; provided that R$_1$ and R$_2$ cannot both be H; or R$_1$ and R$_2$; can be joined to form a saturated ring of 5 or 6 atoms selected from O, S, C or N which can be unsubstituted or substituted optionally on carbon with OH, NR$_5$R$_6$, halogen, C$_{1-4}$alkoxy, C(=O)R$_7$, C$_{1-6}$ alkyl, C$_{1-6}$ alkyl substituted optionally with OH, NR$_5$R$_6$, halogen, C$_{1-4}$ alkoxy, C(=O)R$_7$ or on nitrogen with NR$_5$R$_6$, C$_{1-4}$alkoxy, C(=O)R$_7$, C$_{1-6}$ alkyl or C$_{2-6}$ alkyl substituted optionally with OH, NR$_5$R$_6$, halogen, C$_{1-4}$ alkoxy or C(=O)R$_7$.
R$_3$ is H; halogen; C$_{1-4}$ alkyl; C$_{1-8}$ alkoxy; C$_{1-8}$ alkylthiol; C$_{2-8}$ alkoxy substituted optionally with OH, NR$_5$R$_6$, halogen, C$_{1-4}$ alkoxy or C(=O)R$_7$; C$_{1-4}$ alkyl substituted optionally with R$_4$; or R$_1$ and R$_3$ can be joined together with carbon atoms to form a ring of from 5 to 7 members in wbich said carbon atoms can be unsubstituted or substituted optionally with R$_4$.
R$_4$ is OH; C$_{1-4}$ alkyl unsubstituted or substituted optionally with OH, NR$_5$R$_6$ halogen, C$_{1-4}$ alkoxy or C(=O) R$_7$; C$_{1-4}$ alkoxy; C$_{2-4}$ alkoxy substituted optionally with OH, NR$_5$R$_6$, halogen, C$_{1-4}$ alkoxy or C(=O)R$_7$, NR$_5$R$_6$ phenyl, or heteroaryl, unsubstituted or substituted optionally vith OH, (CH$_2$)$_n$NR$_5$R$_6$, halogen, C$_{1-4}$ alkoxy, C$_{1-4}$ haloalkyoxy, C(=O)R$_7$, S(=O)$_m$R$_8$ or SO$_2$NR$_5$R$_6$, wherein m is 0–2 and n is 0–2;
provided that when R$_3$ is in the 4 position and is H or halogen then R$_1$ and R$_2$ are not H, C$_{1-6}$ alkyl substituted optionally with OH, C$_{1-6}$ alkoxy, C$_{2-6}$ alkoxycarbonyl, nor are they joined to form a 5, 6 or 7 member ring, saturated or unsaturated, comprised of atoms selected optionally from C, O, S, N in which said nitrogen, when saturated is substituted optionally with H or C$_{1-6}$ alkyl or in which said carbon is substituted optionally with C$_{1-6}$ alkyl, C$_{1-6}$ alkoxy or OH and when R$_3$ is in the 5 position and is H, Cl, Br, or C$_{1-3}$ alkyl then neither R$_1$ nor R$_2$ can be H or C$_{1-4}$ alkyl.

$R_5$ and $R_6$ are the same or different and are H; $C_{1-4}$ alkyl; $C_{2-4}$ alkyl substituted optionally with OH, halogen, $C_{1-4}$ alkoxy or C(=O)$R_7$; $C_{1-4}$ alkoxy $C_{2-4}$ alkoxy substituted optionally with OH, halogen; $C_{1-4}$ alkoxy or C(=O)$R_7$; $C_{3-7}$ alkenyl unsubstituted or substituted optionally with OH; $NR_5R_6$, or $C_{1-4}$alkoxy; $C_{3-7}$alkynyl unsubstituted or substituted optionally with OH, $NR_5R_6$, or $C_{1-4}$alkoxy; $C_{1-2}$alkyl$C_{1-3}$cycloalkyl or $R_5$ and $R_6$ can be joined to form a ring of 5 or 6 atoms selected from O, S, C or N which can be unsubstituted or substituted optionally on carbon with OH, (=O), halogen, $C_{1-4}$; alkoxy, C(=O)$R_7$, $C_{1-6}$ alkyl, $C_{1-6}$ alkyl substituted optionally with OH, halogen, $C_{1-4}$ alkoxy C(=O)$R_7$ or on nitrogen with $C_{1-4}$ alkoxy, C(=O)$R_7$ S(=O)$_m R_8$, $C_{1-6}$ alkyl or $C_{2-6}$ alkyl substituted optionally with OH, halogen, $C_{1-4}$ alkoxy, C(=O)$R_7$ or on sulfur by (=O)$_m$ wherein m is 0–2.

$R_7$ is $C_{1-8}$ alkyl; $C_{1-8}$ alkyl substituted optionally with OH, $NR_5R_6$, halogen, $C_{1-4}$ alkoxy or C(=O)$R_9$, $C_{1-4}$alkoxy; $C_{2-4}$ alkoxy substituted optionally with OH, $NR_5R_6$, halogen or $C_{1-4}$ alkoxy; or $NR_5R_6$.

$R_8$ is $C_{1-4}$ alkyl; $C_{2-4}$ alkyl substituted optionally with OH, $NR_5R_6$, halogen, $C_{1-4}$ alkoxy or C(=O)$R_7$.

$R_9$ is $C_{1-4}$ alkyl; $C_{1-4}$ alkoxy amino, $C_{1-3}$ alkylamino, or di-$C_{1-3}$ alkylamino; and G is C(=O) or $SO_2$.

The compounds of formula II are described in and prepared by methods set forth in U.S. Pat. No. 5,153,192, the disclosure of which is hereby incorporated by reference.

Preferred compounds of formula II include compounds of the formula

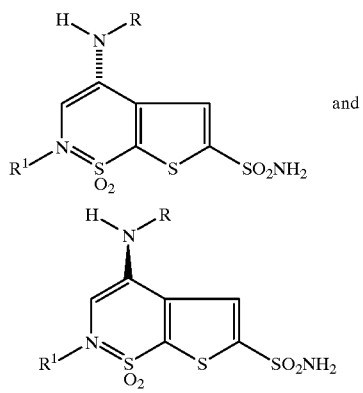

and wherein R is selected from —CH$_2$CH$_3$ or —CH$_2$CH$_2$CH$_3$ and $R^1$ is selected from CH$_3$O(CH$_2$)$_{2-4}$ or a pharmaceutically acceptable salt thereof.

The present invention is based upon the discovery that CAIs when administered topically can resolve macular edemas of various causes. It was found that a patient was quickly able to improve visual acuity as measured by an increase in the number of lines the patient was able to read on the standard eye chart after 40 days of topical treatment with a CAI.

Research was done using TRUSOPT®, a particular carbonic anhydrase inhibitor. It is a known compound useful for the reduction of intraocular pressure as described in U.S. Pat. No. 4,797,413.

The CAI used is preferably administered in the form of ophthalmic pharmaceutical compositions adapted for topical administration to the eye such as solutions, ointments or as a solid insert. Formulations of this compound may contain from 0.01 to 5% and especially 0.5 to 2% of medicament. Higher dosages as, for example, about 10% or lower dosages can be employed provided the dose is effective in increasing blood flow velocity. For a single dose, from between 0.001 to 5.0 mg, preferably 0.005 to 2.0 mg, and especially 0.005 to 1.0 mg of the compound is applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Del. under the name KLUCEL™ such as KLUCEL HF, HWF, MF, GF, JF, LF and EF which are intended for food of pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX™ a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL™ (carboxyvinyl polymer) of B. F. Goodrich and Co. designated as grades 934,940 and 941.

It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size to readily fit into the eye. For example, castings or compression molded films having a thickness of about 0.25 mm to 15.0 mm can be subdivided to obtain suitable inserts. Rectangular segments of the cast or compressed film having a thickness between about 0.5 and 1.5 mm can be cut to afford shapes such as rectangular plates of 4×5–20 mm or ovals of comparable size. Similarly, extruded rods having a diameter between about 0.5 and 1.5 mm can be cut into suitable sections to provide the desired amount of polymer. For example, rods of 1.0 to 1.5 mm in diameter and about 20 mm long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from about 0.001 to about 5% by weight of solid insert, and preferably about 0.1 to about 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between about 5.5 to about 8.0 and especially about 7 to about 8; usually up to about 2% by weight of polymer. The insert may contain from about 1 mg to about 100 mg of water soluble polymer, more particularly from about 5 to about 50 mg and especially from about 5 to about 20 mg. The medicament is present from about 0.1 to about 25% by weight of insert.

The claimed use of topical carbonic anhydrase inhibitiors to treat and prevent macular edema has been the subject of a study to determine whether TRUSOPT® drops were effective as a treatment for cystoid macular edema. In the study, a subject with cystoid macular edema in both eyes was administered TRUSOPT® eye drops twice daily as monotherapy. At the pre-treatment fluorescein angiography examination, the patient presented in the early transit a diffuse leakage of dye out of ectatic retinal capillaries widespread over the posterior pole inducing an intensive fuzzy fluorescence. During midtransit, filling of midsized retinal foveal cycts occurred. After 40 days, the patient underwent fluorescein angiography to determine if the therapy had any effect on the edema. The post-treatment fluorescein angiography presented reduced leakage and primarily small and packed aggregate retinal cysts as well as a reading acuity improvement of four lines in the Snellen chart.

What is claimed is:

1. A method for treating macular edema which comprises topically administering to the eye of a patient in need of such treatment a topical carbonic anhydrase inhibitor in sufficient amounts to improve visual acuity by resolving said macular edemas.

2. The method according to claim 1 wherein the carbonic anhydrase inhibitor is a compound of the formula

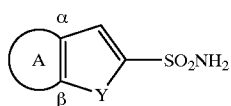 (I)

wherein A together with the two carbon atoms denoted as α and β is the group

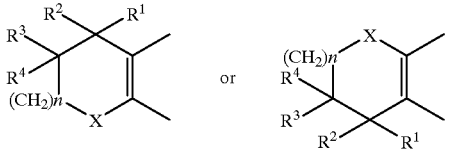 or wherein:
X is —S—, —SO—, —SO$_2$— or —CH$_2$—;
Y is —S—, —O—, or —NR$^3$— wherein R$^3$ is hydrogen, C$_{1-3}$alkyl, or benzyl;
n is 1 or 2;
R$^1$, R$^2$, R$^3$, R$^4$ are independently selected from:
1) hydrogen,
2) OR$^5$ wherein R$^5$ is:
   a) hydrogen,
   b) C$_{1-5}$ alkyl, either unsubstituted or substituted with —OH, or

wherein R$^6$ and R$^7$ are independently hydrogen or C$_{1-5}$ alkyl, or joined together form a heterocycle with the nitrogen to which they are attached such as piperidino, morpholino, or piperazino,
   c) C$_{1-5}$ alkanoyl, either unsubstituted or substituted with —OH, —NR$^6$R$^7$, —NH—COR$^8$ or —COR$^8$ wherein R$^8$ is —OH, —NR$^6$R$^7$ or C$_{1-5}$ alkoxy,
   d) —CO—R$^9$, wherein R$^9$ is —NR$^6$R$^7$ or a 5- or 6-membered aromatic heterocycle such as pyridyl, imidazolyl, pyrazinyl, thiazolyl, thienyl, or oxazolyl,
3) —NR$^6$R$^7$,
4) —NHR$^{10}$ wherein R$^{10}$ is:
   a) —SO$_2$NR$^6$R$^7$,
   b) —SO$_2$R$^{11}$, wherein R$^{11}$ is C$_{1-5}$ alkyl, or
   c) —CONR$^6$R$^7$,
5) C$_{1-5}$ alkyl, either unsubstituted or substituted with
   a) —OR$^5$,
   b) —CN,
   c) —NR$^6$R$^7$, or
   d) —COR$^8$,
6) —SO$_2$R$^{11}$,
7) —SO$_2$NR$^6$R$^7$, or
8) -halo, such as chloro, bromo or fluoro;
R$^1$ and R$^3$, or R$^2$ and R$^4$ taken together represent a double bond;
R$^1$ and R$^2$, or R$^3$ and R$^4$ taken together represent
1) =O, or
2) =NOR$^{12}$ wherein R$^{12}$ is hydrogen or C$_{1-3}$alkyl; and one of the —CH$_2$— groups of —(CH$_2$)$_n$— can be substituted with —COR$^8$, —CH$_2$R$^8$, or —CH$_2$COR$^8$;
or a pharmaceutically acceptable salt thereof.

3. The method according to claim 1 wherein the carbonic anhydrase inhibitor is a compound of the formula

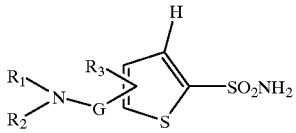 (II)

or a pharmaceutically acceptable salt thereof wherein;
R$_1$ is H; C$_{1-4}$ alkyl; C$_{2-4}$ alkyl substdtuted optionally with OH, halogen, C$_{1-4}$ alkoxy or C(=O)R$_7$;
R$_2$ is H; C$_{1-8}$ alkyl; C$_{2-8}$ alkyl substituted with OH, NR$_5$R$_6$, halogen, C$_{1-4}$ alkoxy or C(=O)R$_7$; C$_{3-7}$ alkenyl unsubstituted or substituted optionally with OH, NR$_5$R$_6$, or C$_{1-4}$ alkoxy; C$_{3-7}$ alkynyl unsubstituted or substituted optionally with OH, NR$_5$R$_6$, or C$_{1-4}$ alkoxy; C$_{1-3}$ alkyl substituted with phenyl or heteroaryl which can be unsubstituted or substituted optionally with OH, C(H$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2; C$_{2-4}$ alkoxy substituted optionally with NR$_5$R$_6$, halogen, C$_{1-4}$ alkoxy, or C(=O)R$_7$; phenyl, or heteroaryl, unsubstituted or substituted optionally with OH, (CH$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2; provided that R$_1$ and R$_2$ cannot both be H; or R$_1$ and R$_2$; can be joined to form a saturated ring of 5 or 6 atoms selected from O, S, C or N which can be unsubstituted or substituted optionally on carbon with OH, NR$_5$R$_6$, halogen, C$_{1-4}$alkoxy, C(=O)R$_7$, C$_{1-6}$ alkyl, C$_{1-6}$ alkyl substituted optionally with OH, NR$_5$R$_6$, halogen, C$_{1-4}$ alkoxy, C(=O)R$_7$ or on nitrogen with NR$_5$R$_6$, C$_{1-4}$alkoxy, C(=O)R$_7$, C$_{1-6}$ alkyl or C$_{2-6}$ alkyl substituted optionally with OH, NR$_5$R$_6$, halogen, C$_{1-4}$ alkoxy or C(=O)R$_7$;
R$_3$ is H; halogen; C$_{1-4}$ alkyl; C$_{1-8}$ alkoxy; C$_{1-8}$ alkylthiol; C$_{2-8}$ alkoxy substituted optionally with OH, NR$_5$R$_6$, halogen, C$_{1-4}$ alkoxy or C(=O)R$_7$; C$_{1-4}$ alkyl substituted optionally with R$_4$; or R$_1$ and R$_3$ can be joined together with carbon atoms to form a ring of from 5 to 7 members in wbich said carbon atoms can be unsubstituted or substituted optionally with R$_4$;
R$_4$ is OH; C$_{1-4}$ alkyl unsubstituted or substituted optionally with OH, NR$_5$R$_6$ halogen, C$_{1-4}$ alkoxy or C(=O)R$_7$; C$_{1-4}$ alkoxy; C$_{2-4}$ alkoxy substituted optionally with OH, NR$_5$R$_6$, halogen, C$_{1-4}$ alkoxy or C(=O)R$_7$, NR$_5$R$_6$ phenyl, or heteroaryl, unsubstituted or substituted optionally vith OH, (CH$_2$)$_n$NR$_5$R$_6$, halogen, C$_{1-4}$ alkoxy, C$_{1-4}$ haloalkyoxy, C(=O)R$_7$, S(=O)$_m$R$_8$ or SO$_2$NR$_5$R$_6$, wherein m is 0–2 and n is 0–2;
provided that when R$_3$ is in the 4 position and is H or halogen then R$_1$ and R$_2$ are not H, C$_{1-6}$ alkyl substituted optionally with OH, C$_{1-6}$ alkoxy, C$_{2-6}$ alkoxycarbonyl, nor are they joined to form a 5, 6 or 7 member ring, saturated or unsaturated, comprised of atoms selected optionally from C, O, S, N in which said nitrogen, when saturated is substituted optionally with H or C$_{1-6}$ alkyl or in which said carbon is substituted optionally with C$_{1-6}$ alkyl, C$_{1-6}$ alkoxy or OH and when R$_3$ is in the 5 position and is H, Cl, Br, or C$_{1\ 3}$ alkyl then neither R$_1$ nor R$_2$ can be H or C$_{1-4}$ alkyl;

R₅ and R₆ are the same or different and are H; $C_{1-4}$ alkyl; $C_{2-4}$ alkyl substituted optionally with OH, halogen, $C_{1-4}$ alkoxy or $C(=O)R_7$; $C_{1-4}$ alkoxy $C_{2-4}$ alkoxy substituted optionally with OH, halogen; $C_{1-4}$ alkoxy or $C(=O)R_7$; $C_{3-7}$ alkenyl unsubstituted or substituted optionally with OH; $NR_5R_6$, or $C_{1-4}$alkoxy; $C_{3-7}$alkynyl unsubstituted or substituted optionally with OH, $NR_5R_6$, or $C_{1-4}$alkoxy; $C_{1-2}$alkyl$C_{1-3}$cycloalkyl or R₅ and R₆ can be joined to form a ring of 5 or 6 atoms selected from O, S, C or N which can be unsubstituted or substituted optionally on carbon with OH, (=O), halogen, $C_{1-4}$; alkoxy, $C(=O)R_7$, $C_{1-6}$ alkyl, $C_{1-6}$ alkyl substituted optionally with OH, halogen, $C_{1-4}$ alkoxy $C(=O)R_7$ or on nitrogen with $C_{1-4}$ alkoxy, $C(=O)R_7$ $S(=O)_mR_8$, $C_{1-6}$ alkyl or $C_{2-6}$ alkyl substituted optionally with OH, halogen, $C_{1-4}$ alkoxy, $C(=O)R_7$ or on sulfur by $(=O)_m$ wherein m is 0–2;

R₇ is $C_{1-8}$ alkyl; $C_{1-8}$ alkyl substituted optionally with OH, $NR_5R_6$, halogen, $C_{1-4}$ alkoxy or $C(=O)R_9$, $C_{1-4}$alkoxy; $C_{2-4}$ alkoxy substituted optionally with OH, $NR_5R_6$, halogen or $C_{1-4}$ alkoxy; or $NR_5R_6$;

R₈ is $C_{1-4}$ alkyl; $C_{2-4}$ alkyl substituted optionally with OH, $NR_5R_6$, halogen, $C_{1-4}$ alkoxy or $C(=O)R_7$;

R₉ is $C_{1-4}$ alkyl; $C_{1-4}$ alkoxy amino, $C_{1-3}$ alkylamino, or di-$C_{1-3}$ alkylamino; and G is $C(=O)$ or $SO_2$.

4. The method according to claim 3 wherein the carbonic anhydrase inhibitor is selected from a compound of the formula

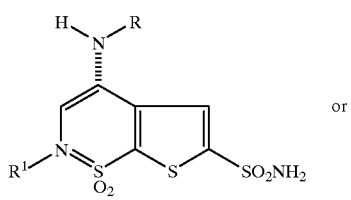

or

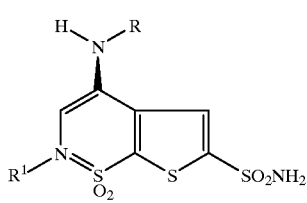

wherein R is selected from —CH₂CH₃ or —CH₂CH₂CH₃ and R¹ is selected from CH₃O(CH₂)₂₋₄ or a pharmaceutically acceptable salt thereof.

5. The method according to claim 1 wherein the carbonic anhydrase inhibitor comprises dorzolamide, acetazolamide and methazolamide.

6. The method according to claim 5 wherein the carbonic anhydrase inhibitor is dorzolamide.

7. A method of preventing macular edema in a patient which comprises topically administering to the eye of a patient in need of such treatment a topical carbonic anhydrase inhibitor in sufficient amounts to substantially prevent or minimize the onset of macular edema in the patient.

8. The method according to claim 7 wherein the carbonic anhydrase inhibitor is a compound of the formula

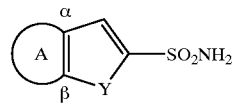

(I)

wherein A together with the two carbon atoms denoted as α and β is the group

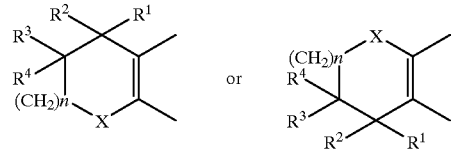

wherein:

X is —S—, —SO—, —SO₂— or —CH₂—;

Y is —S—, —O—, or —NR³— wherein R³ is hydrogen, $C_{1-3}$alkyl, or benzyl;

n is 1 or 2;

R¹, R², R³, R⁴ are independently selected from:
1) hydrogen,
2) OR⁵ wherein R⁵ is:
   a) hydrogen,
   b) $C_{1-5}$ alkyl, either unsubstituted or substituted with —OH, or

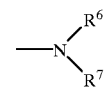

wherein R⁶ and R⁷ are independently hydrogen or $C_{1-5}$ alkyl, or joined together form a heterocycle with the nitrogen to which they are attached such as piperidino, morpholino, or piperazino, c) $C_{1-5}$ alkanoyl, either unsubstituted or substituted with —OH, —NR⁶R⁷, —NH—COR⁸ or —COR⁸ wherein R⁸ is —OH, —NR⁶R⁷ or $C_{1-5}$ alkoxy,
   d) —CO—R⁹, wherein R⁹ is —NR⁶R⁷ or a 5- or 6-membered aromatic heterocycle such as pyridyl, imidazolyl, pyrazinyl, thiazolyl, thienyl, or oxazolyl,
3) —NR⁶R⁷,
4) —NHR¹⁰ wherein R¹⁰ is:
   a) —SO₂NR⁶R⁷,
   b) —SO₂R¹¹, wherein R¹¹ is $C_{1-5}$ alkyl, or
   c) —CONR⁶R⁷,
5) $C_{1-5}$ alkyl, either unsubstituted or substituted with
   a) —OR⁵,
   b) —CN,
   c) —NR⁶R⁷, or
   d) —COR⁸,
6) —SO₂R¹¹,
7) —SO₂NR⁶R⁷, or
8) -halo, such as chloro, bromo or fluoro;

R¹ and R³, or R² and R⁴ taken together represent a double bond;

R¹ and R², or R³ and R⁴ taken together represent
1) =O, or
2) =NOR¹² wherein R¹² is hydrogen or $C_{1-3}$alkyl; and one of the —CH₂— groups of —(CH₂)ₙ— can be substituted with —COR⁸, —CH₂R⁸, or —CH₂COR⁸;

or a pharmaceutically acceptable salt thereof.

9. The method according to claim 7 wherein the carbonic anhydrase inhibitor is a compound of the formula

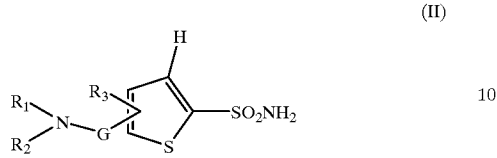

(II)

or a pharmaceutically acceptable salt thereof wherein;

$R_1$ is H; $C_{1-4}$ alkyl; $C_{2-4}$ alkyl substdtuted optionally with OH, halogen, $C_{1-4}$ alkoxy or $C(=O)R_7$;

$R_2$ is H; $C_{1-8}$ alkyl; $C_{2-8}$ alkyl substituted with OH, $NR_5R_6$, halogen, $C_{1-4}$ alkoxy or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-3}$ alkyl substituted with phenyl or heteroaryl which can be unsubstituted or substituted optionally with OH, $C(H_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; $C_{2-4}$ alkoxy substituted optionally with $NR_5R_6$, halogen, $C_{1-4}$ alkoxy, or $C(=O)R_7$; phenyl, or heteroaryl, unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; provided that $R_1$ and $R_2$ cannot both be H; or $R_1$ and $R_2$; can be joined to form a saturated ring of 5 or 6 atoms selected from O, S, C or N which can be unsubstituted or substituted optionally on carbon with OH, $NR_5R_6$, halogen, $C_{1-4}$alkoxy, $C(=O)R_7$, $C_{1-6}$ alkyl, $C_{1-6}$ alkyl substituted optionally with OH, $NR_5R_6$, halogen, $C_{1-4}$ alkoxy, $C(=O)R_7$ or on nitrogen with $NR_5R_6$, $C_{1-4}$alkoxy, $C(=O)R_7$, $C_{1-6}$ alkyl or $C_{2-6}$ alkyl substituted optionally with OH, $NR_5R_6$, halogen, $C_{1-4}$ alkoxy or $C(=O)R_7$;

$R_3$ is H; halogen; $C_{1-8}$ alkyl; $C_{1-8}$ alkoxy; $C_{1-8}$ alkylthiol; $C_{2-8}$ alkoxy substituted optionally with OH, $NR_5R_6$, halogen, $C_{1-4}$ alkoxy or $C(=O)R_7$; $C_{1-4}$ alkyl substituted optionally with $R_4$; or $R_1$ and $R_3$ can be joined together with carbon atoms to form a ring of from 5 to 7 members in wbich said carbon atoms can be unsubstituted or substituted optionally with $R_4$;

$R_4$ is OH; $C_{1-4}$ alkyl unsubstituted or substituted optionally with OH, $NR_5R_6$ halogen, $C_{1-4}$ alkoxy or $C(=O)R_7$; $C_{1-4}$ alkoxy; $C_{2-4}$ alkoxy substituted optionally with OH, $NR_5R_6$, halogen, $C_{1-4}$ alkoxy or $C(=O)R_7$, $NR_5R_6$ phenyl, or heteroaryl, unsubstituted or substituted optionally vith OH, $(CH_2)_nNR_5R_6$, halogen, $C_{1-4}$ alkoxy, $C_{1-4}$ haloalkyoxy, $C(=O)R_7$, $S(=O)_mR_8$ or $SO_2NR_5R_6$, wherein m is 0–2 and n is 0–2;

provided that when $R_3$ is in the 4 position and is H or halogen then $R_1$ and $R_2$ are not H, $C_{1-6}$ alkyl substituted optionally with OH, $C_{1-6}$ alkoxy, $C_{2-6}$ alkoxycarbonyl, nor are they joined to form a 5, 6 or 7 member ring, saturated or unsaturated, comprised of atoms selected optionally from C, O, S, N in which said nitrogen, when saturated is substituted optionally with H or $C_{1-6}$ alkyl or in which said carbon is substituted optionally with $C_{1-6}$ alkyl, $C_{1-6}$ alkoxy or OH and when $R_3$ is in the 5 position and is H, Cl, Br, or $C_{1\ 3}$ alkyl then neither $R_1$ nor $R_2$ can be H or $C_{1-4}$ alkyl;

$R_5$ and $R_6$ are the same or different and are H; $C_{1-4}$ alkyl; $C_{2-4}$ alkyl substituted optionally with OH, halogen, $C_{1-4}$ alkoxy or $C(=O)R_7$; $C_{1-4}$ alkoxy $C_{2-4}$ alkoxy substituted optionally with OH, halogen; $C_{1-4}$ alkoxy or $C(=O)R_7$; $C_{3-7}$ alkenyl unsubstituted or substituted optionally with OH; $NR_5R_6$, or $C_{1-4}$alkoxy; $C_{3-7}$alkynyl unsubstituted or substituted optionally with OH, $NR_5R_6$, or $C_{1-4}$alkoxy; $C_{1-2}$alkyl$C_{1-3}$cycloalkyl or $R_5$ and $R_6$ can be joined to form a ring of 5 or 6 atoms selected from O, S, C or N which can be unsubstituted or substituted optionally on carbon with OH, (=O), halogen, $C_{1-4}$; alkoxy, $C(=O)R_7$, $C_{1-6}$ alkyl, $C_{1-6}$ alkyl substituted optionally with OH, halogen, $C_{1-4}$ alkoxy $C(=O)R_7$ or on nitrogen with $C_{1-4}$ alkoxy, $C(=O)R_7$ $S(=O)_mR_8$, $C_{1-6}$ alkyl or $C_{2-6}$ alkyl substituted optionally with OH, halogen, $C_{1-4}$ alkoxy, $C(=O)R_7$ or on sulfur by $(=O)_m$ wherein m is 0–2;

$R_7$ is $C_{1-8}$ alkyl; $C_{1-8}$ alkyl substituted optionally with OH, $NR_5R_6$, halogen, $C_{1-4}$ alkoxy or $C(=O)R_9$, $C_{1-4}$alkoxy; $C_{2-4}$ alkoxy substituted optionally with OH, $NR_5R_6$, halogen or $C_{1-4}$ alkoxy; or $NR_5R_6$;

$R_8$ is $C_{1-4}$ alkyl; $C_{2-4}$ alkyl substituted optionally with OH, $NR_5R_6$, halogen, $C_{1-4}$ alkoxy or $C(=O)R_7$;

$R_9$ is $C_{1-4}$ alkyl; $C_{1-4}$ alkoxy amino, $C_{1-3}$ alkylamino, or di-$C_{1-3}$ alkylamino; and G is $C(=O)$ or $SO_2$.

10. The method according to claim 9 wherein the carbonic anhydrase inhibitor is selected from a compound of the formula

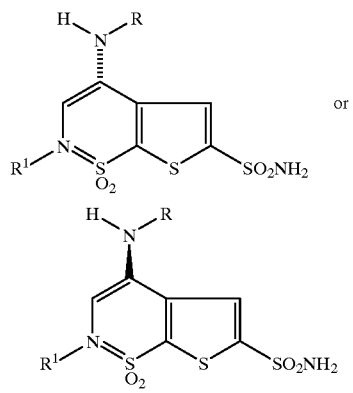

wherein R is selected from —CH₂CH₃ or —CH₂CH₂CH₃ and $R^1$ is selected from $CH_3O(CH_2)_{2-4}$ or a pharmaceutically acceptable salt thereof.

11. The method according to claim 7 wherein the carbonic anhydrase inhibitor comprises dorzolamide, acetazolamide and methazolamide.

12. The method according to claim 11 wherein the carbonic anhydrase inhibitor is dorzolamide.

13. A method of treating age-related macular degeneration which comprises topically administering to the eye of a patient in need of such treatment a topical carbonic anhydrase inhibitor in sufficient amounts to inhibit the onset or progression of ophthalmic problems caused by said macular degeneration.

14. The method according to claim 13 wherein the carbonic anhydrase inhibitor comprises dorzolamide, acetazolamide and methazolamide.

15. The method according to claim 13 wherein the carbonic anhydrase inhibitor is dorzolamide.

16. The method according to claim 13 wherein the carbonic anhydrase inhibitor is a compound of the formula

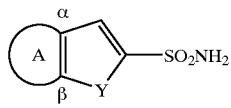

(I)

wherein A together with the two carbon atoms denoted as α and β is the group

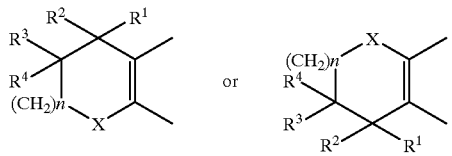

wherein:
X is —S—, —SO—, —SO$_2$— or —CH$_2$—;
Y is —S—, —O—, or —NR$^3$— wherein R$^3$ is hydrogen, C$_{1-3}$alkyl, or benzyl;
n is 1 or 2;
R$^1$, R$^2$, R$^3$, R$^4$ are independently selected from:
 1) hydrogen,
 2) OR$^5$ wherein R$^5$ is:
  a) hydrogen,
  b) C$_{1-5}$ alkyl, either unsubstituted or substituted with —OH, or

wherein R$^6$ and R$^7$ are independently hydrogen or C$_{1-5}$ alkyl, or joined together form a heterocycle with the nitrogen to which they are attached such as piperidino, morpholino, or piperazino,
  c) C$_{1-5}$ alkanoyl, either unsubstituted or substituted with —OH, —NR$^6$R$^7$, —NH—COR$^8$ or —COR$^8$ wherein R$^8$ is —OH, —NR$^6$R$^7$ or C$_{1-5}$ alkoxy,
  d) —CO—R$^9$, wherein R$^9$ is —NR$^6$R$^7$ or a 5- or 6-membered aromatic heterocycle such as pyridyl, imidazolyl, pyrazinyl, thiazolyl, thienyl, or oxazolyl,
 3) —NR$^6$R$^7$,
 4) —NHR$^{10}$ wherein R$^{10}$ is:
  a) —SO$_2$NR$^6$R$^7$,
  b) —SO$_2$R$^{11}$, wherein R$^{11}$ is C$_{1-5}$ alkyl, or
  c) —CONR$^6$R$^7$,
 5) C$_{1-5}$ alkyl, either unsubstituted or substituted with
  a) —OR$^5$,
  b) —CN,
  c) —NR$^6$R$^7$, or
  d) —COR$^8$,
 6) —SO$_2$R$^{11}$,
 7) —SO$_2$NR$^6$R$^7$, or
 8) -halo, such as chloro, bromo or fluoro;
R$^1$ and R$^3$, or R$^2$ and R$^4$ taken together represent a double bond;
R$^1$ and R$^2$, or R$^3$ and R$^4$ taken together represent
 1) =O, or
 2) =NOR$^{12}$ wherein R$^{12}$ is hydrogen or C$_{1-3}$alkyl; and one of the —CH$_2$— groups of —(CH$_2$)$_n$— can be substituted with —COR$^8$, —CH$_2$R$^8$, or —CH$_2$COR$^8$;
or a pharmaceutically acceptable salt thereof.

17. The method according to claim 13 wherein the carbonic anhydrase inhibitor is a compound of the formula

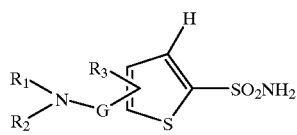

(II)

or a pharmaceutically acceptable salt thereof wherein;
 R$_1$ is H; C$_{1-4}$ alkyl; C$_{2-4}$ alkyl substdtuted optionally with OH, halogen, C$_{1-4}$ alkoxy or C(=O)R$_7$;
 R$_2$ is H; C$_{1-8}$ alkyl; C$_{2-8}$ alkyl substituted with OH, NR$_5$R$_6$, halogen, C$_{1-4}$ alkoxy or C(=O)R$_7$; C$_{3-7}$ alkenyl unsubstituted or substituted optionally with OH, NR$_5$R$_6$, or C$_{1-4}$ alkoxy; C$_{3-7}$ alkynyl unsubstituted or substituted optionally with OH, NR$_5$R$_6$, or C$_{1-4}$ alkoxy; C$_{1-3}$ alkyl substituted with phenyl or heteroaryl which can be unsubstituted or substituted optionally with OH, C(H$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2; C$_{2-4}$ alkoxy substituted optionally with NR$_5$R$_6$, halogen, C$_{1-4}$ alkoxy, or C(=O)R$_7$; phenyl, or heteroaryl, unsubstituted or substituted optionally with OH, (CH$_2$)$_n$NR$_5$R$_6$, halogen, C$_{1-4}$ alkoxy, C$_{1-4}$ haloalkoxy, C(=O)R$_7$, S(=O)$_m$R$_8$ or SO$_2$NR$_5$R$_6$, wherein m is 0–2 and n is 0–2; provided that R$_1$ and R$_2$ cannot both be H; or R$_1$ and R$_2$; can be joined to form a saturated ring of 5 or 6 atoms selected from O, S, C or N which can be unsubstituted or substituted optionally on carbon with OH, NR$_5$R$_6$, halogen, C$_{1-4}$alkoxy, C(=O)R$_7$, C$_{1-6}$ alkyl, C$_{1-6}$ alkyl substituted optionally with OH, NR$_5$R$_6$, halogen, C$_{1-4}$ alkoxy, C(=O)R$_7$ or on nitrogen with NR$_5$R$_6$, C$_{1-4}$alkoxy, C(=O)R$_7$, C$_{1-6}$ alkyl or C$_{2-6}$ alkyl substituted optionally with OH, NR$_5$R$_6$, halogen, C$_{1-4}$ alkoxy or C(=O)R$_7$;
 R$_3$ is H; halogen; C$_{1-4}$ alkyl; C$_{1-8}$ alkoxy; C$_{1-8}$ alkylthiol; C$_{2-8}$ alkoxy substituted optionally with OH, NR$_5$R$_6$, halogen, C$_{1-4}$ alkoxy or C(=O)R$_7$; C$_{1-4}$ alkyl substituted optionally with R$_4$; or R$_1$ and R$_3$ can be joined together with carbon atoms to form a ring of from 5 to 7 members in wbich said carbon atoms can be unsubstituted or substituted optionally with R$_4$;
 R$_4$ is OH; C$_{1-4}$ alkyl unsubstituted or substituted optionally with OH, NR$_5$R$_6$ halogen, C$_{1-4}$ alkoxy or C(=O) R$_7$; C$_{1-4}$ alkoxy; C$_{2-4}$ alkoxy substituted optionally with OH, NR$_5$R$_6$, halogen, C$_{1-4}$ alkoxy or C(=O)R$_7$, NR$_5$R$_6$ phenyl, or heteroaryl, unsubstituted or substituted optionally vith OH, (CH$_2$)$_n$NR$_5$R$_6$, halogen, C$_{1-4}$ alkoxy, C$_{1-4}$ haloalkyoxy, C(=O)R$_7$, S(=O)$_m$R$_8$ or SO$_2$NR$_5$R$_6$, wherein m is 0–2 and n is 0–2;
 provided that when R$_3$ is in the 4 position and is H or halogen then R$_1$ and R$_2$ are not H, C$_{1-6}$ alkyl substituted optionally with OH, C$_{1-6}$ alkoxy, C$_{2-6}$ alkoxycarbonyl, nor are they joined to form a 5, 6 or 7 member ring, saturated or unsaturated, comprised of atoms selected optionally from C, O, S, N in which said nitrogen, when saturated is substituted optionally with H or C$_{1-6}$ alkyl or in which said carbon is substituted optionally with C$_{1-6}$ alkyl, C$_{1-6}$ alkoxy or OH and when R$_3$ is in the 5 position and is H, Cl, Br, or C$_{1\ 3}$ alkyl then neither R$_1$ nor R$_2$ can be H or C$_{1-4}$ alkyl;

$R_5$ and $R_6$ are the same or different and are H; $C_{1-4}$ alkyl; $C_{2-4}$ alkyl substituted optionally with OH, halogen, $C_{1-4}$ alkoxy or $C(=O)R_7$; $C_{1-4}$ alkoxy $C_{2-4}$ alkoxy substituted optionally with OH, halogen; $C_{1-4}$ alkoxy or $C(=O)R_7$; $C_{3-7}$ alkenyl unsubstituted or substituted optionally with OH; $NR_5R_6$, or $C_{1-4}$-alkoxy; $C_{3-7}$alkynyl unsubstituted or substituted optionally with OH, $NR_5R_6$, or $C_{1-4}$ alkoxy; $C_{1-2}$alkyl$C_{1-3}$cycloalkyl or $R_5$ and $R_6$ can be joined to form a ring of 5 or 6 atoms selected from O, S, C or N which can be unsubstituted or substituted optionally on carbon with OH, (=O), halogen, $C_{1-4}$; alkoxy, $C(=O)R_7$, $C_{1-6}$ alkyl, $C_{1-6}$ alkyl substituted optionally with OH, halogen, $C_{1-4}$ alkoxy $C(=O)R_7$ or on nitrogen with $C_{1-4}$ alkoxy, $C(=O)R_7$ $S(=O)_mR_8$, $C_{1-6}$ alkyl or $C_{2-6}$ alkyl substituted optionally with OH, halogen, $C_{1-4}$ alkoxy, $C(=O)R_7$ or on sulfur by $(=O)_m$ wherein m is 0–2;

$R_7$ is $C_{1-8}$ alkyl; $C_{1-8}$ alkyl substituted optionally with OH, $NR_5R_6$, halogen, $C_{1-4}$ alkoxy or $C(=O)R_9$, $C_{1-4}$alkoxy; $C_{2-4}$ alkoxy substituted optionally with OH, $NR_5R_6$, halogen or $C_{1-4}$ alkoxy; or $NR_5R_6$;

$R_8$ is $C_{1-4}$ alkyl; $C_{2-4}$ alkyl substituted optionally with OH, $NR_5R_6$, halogen, $C_{1-4}$ alkoxy or $C(=O)R_7$;

$R_9$ is $C_{1-4}$ alkyl; $C_{1-4}$ alkoxy amino, $C_{1-3}$ alkylamino, or di-$C_{1-3}$ alkylamino; and G is $C(=O)$ or $SO_2$.

18. The method according to claim 13 wherein the carbonic anhydrase inhibitor is selected from a compound of the formula

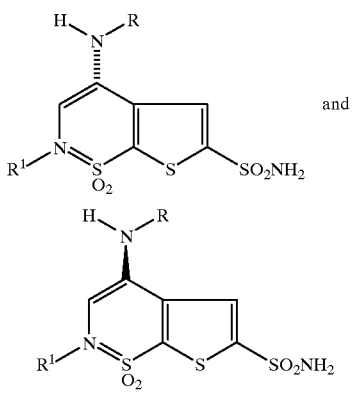

and wherein R is selected from —$CH_2CH_3$ or —$CH_2CH_2CH_3$ and $R^1$ is selected from $CH_3O(CH_2)_{2-4}$ or a pharmaceutically acceptable salt thereof.

19. A method for preventing age-related macular degeneration which comprises applying to the eye an effective amount of a topical carbonic anhydrase inhibitor.

20. The method according to claim 19 wherein the carbonic anhydrase inhibitor comprises dorzolamide, acetazolamide and methazolamide.

21. The method according to claim 20 wherein the carbonic anhydrase inhibitor is dorzolamide.

22. The method according to claim 19 wherein the carbonic anhydrase inhibitor is a compound of the formula

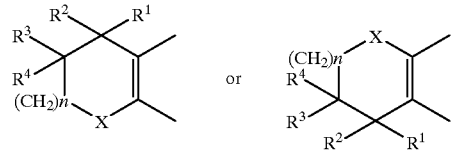

(I)

wherein A together with the two carbon atoms denoted as $\alpha$ and $\beta$ is the group

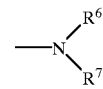

wherein:

X is —S—, —SO—, —$SO_2$— or —$CH_2$—;

Y is —S—, —O—, or —$NR^3$— wherein $R^3$ is hydrogen, $C_{1-3}$alkyl, or benzyl;

n is 1 or 2;

$R^1$, $R^2$, $R^3$, $R^4$ are independently selected from:
1) hydrogen,
2) $OR^5$ wherein $R^5$ is:
   a) hydrogen,
   b) $C_{1-5}$ alkyl, either unsubstituted or substituted with —OH, or $$-N\begin{matrix}R^6\\R^7\end{matrix}$$

wherein $R^6$ and $R^7$ are independently hydrogen or $C_{1-5}$ alkyl, or joined together form a heterocycle with the nitrogen to which they are attached such as piperidino, morpholino, or piperazino,
   c) $C_{1-5}$ alkanoyl, either unsubstituted or substituted with —OH, —$NR^6R^7$, —NH—$COR^8$ or —$COR^8$ wherein $R^8$ is —OH, —$NR^6R^7$ or $C_{1-5}$ alkoxy,
   d) —CO—$R^9$, wherein $R^9$ is —$NR^6R^7$ or a 5- or 6-membered aromatic heterocycle such as pyridyl, imidazolyl, pyrazinyl, thiazolyl, thienyl, or oxazolyl, 3) —$NR^6R^7$,
4) —$NHR^{10}$ wherein $R^{10}$ is:
   a) —$SO_2NR^6R^7$,
   b) —$SO_2R^{11}$, wherein $R^{11}$ is $C_{1-5}$ alkyl, or
   c) —$CONR^6R^7$,
5) $C_{1-5}$ alkyl, either unsubstituted or substituted with
   a) —$OR^5$,
   b) —CN,
   c) —$NR^6R^7$, or
   d) —$COR^8$,
6) —$SO_2R^{11}$,
7) —$SO_2NR^6R^7$, or
8) -halo, such as chloro, bromo or fluoro;

$R^1$ and $R^3$, or $R^2$ and $R^4$ taken together represent a double bond;

$R^1$ and $R^2$, or $R^3$ and $R^4$ taken together represent
1) =O, or
2) =$NOR^{12}$ wherein $R^{12}$ is hydrogen or $C_{1-3}$alkyl; and
one of the —$CH_2$— groups of —$(CH_2)_n$— can be substituted with —COR⁸, —CH₂R⁸, or —CH₂COR⁸;
or a pharmaceutically acceptable salt thereof.

23. The method according to claim 19 wherein the carbonic anhydrase inhibitor is a compound of the formula

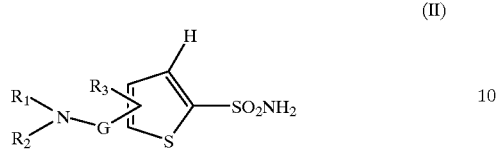

(II)

or a pharmaceutically acceptable salt thereof wherein;
$R_1$ is H; $C_{1-4}$ alkyl; $C_{2-4}$ alkyl substdtuted optionally with OH, halogen, $C_{1-4}$ alkoxy or $C(=O)R_7$;

$R_2$ is H; $C_{1-8}$ alkyl; $C_{2-8}$ alkyl substituted with OH, $NR_5R_6$, halogen, $C_{1-4}$ alkoxy or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-3}$ alkyl substituted with phenyl or heteroaryl which can be unsubstituted or substituted optionally with OH, $C(H_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; $C_{2-4}$ alkoxy substituted optionally with $NR_5R_6$, halogen, $C_{1-4}$ alkoxy, or $C(=O)R_7$; phenyl, or heteroaryl, unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; provided that $R_1$ and $R_2$ cannot both be H; or $R_1$ and $R_2$; can be joined to form a saturated ring of 5 or 6 atoms selected from O, S, C or N which can be unsubstituted or substituted optionally on carbon with OH, $NR_5R_6$, halogen, $C_{1-4}$alkoxy, $C(=O)R_7$, $C_{1-6}$ alkyl, $C_{1-6}$ alkyl substituted optionally with OH, $NR_5R_6$, halogen, $C_{1-4}$ alkoxy, $C(=O)R_7$ or on nitrogen with $NR_5R_6$, $C_{1-4}$alkoxy, $C(=O)R_7$, $C_{1-6}$ alkyl or $C_{2-6}$ alkyl substituted optionally with OH, $NR_5R_6$, halogen, $C_{1-4}$ alkoxy or $C(=O)R_7$;

$R_3$ is H; halogen; $C_{1-4}$ alkyl; $C_{1-8}$ alkoxy; $C_{1-8}$ alkylthiol; $C_{2-8}$ alkoxy substituted optionally with OH, $NR_5R_6$, halogen, $C_{1-4}$ alkoxy or $C(=O)R_7$; $C_{1-4}$ alkyl substituted optionally with $R_4$; or $R_1$ and $R_3$ can be joined together with carbon atoms to form a ring of from 5 to 7 members in wbich said carbon atoms can be unsubstituted or substituted optionally with $R_4$;

$R_4$ is OH; $C_{1-4}$ alkyl unsubstituted or substituted optionally with OH, $NR_5R_6$ halogen, $C_{1-4}$ alkoxy or $C(=O)R_7$; $C_{1-4}$ alkoxy; $C_{2-4}$ alkoxy substituted optionally with OH, $NR_5R_6$, halogen, $C_{1-4}$ alkoxy or $C(=O)R_7$, $NR_5R_6$ phenyl, or heteroaryl, unsubstituted or substituted optionally vith OH, $(CH_2)_nNR_5R_6$, halogen, $C_{1-4}$ alkoxy, $C_{1-4}$ haloalkyoxy, $C(=O)R_7$, $S(=O)_mR_8$ or $SO_2NR_5R_6$, wherein m is 0–2 and n is 0–2;

provided that when $R_3$ is in the 4 position and is H or halogen then $R_1$ and $R_2$ are not H, $C_{1-6}$ alkyl substituted optionally with OH, $C_{1-6}$ alkoxy, $C_{2-6}$ alkoxycarbonyl, nor are they joined to form a 5, 6 or 7 member ring, saturated or unsaturated, comprised of atoms selected optionally from C, O, S, N in which said nitrogen, when saturated is substituted optionally with H or $C_{1-6}$ alkyl or in which said carbon is substituted optionally with $C_{1-6}$ alkyl, $C_{1-6}$ alkoxy or OH and when $R_3$ is in the 5 position and is H, Cl, Br, or $C_{1-3}$ alkyl then neither $R_1$ nor $R_2$ can be H or $C_{1-4}$ alkyl;

$R_5$ and $R_6$ are the same or different and are H; $C_{1-4}$ alkyl; $C_{2-4}$ alkyl substituted optionally with OH, halogen, $C_{1-4}$ alkoxy or $C(=O)R_7$; $C_{1-4}$ alkoxy $C_{2-4}$ alkoxy substituted optionally with OH, halogen; $C_{1-4}$ alkoxy or $C(=O)R_7$; $C_{3-7}$ alkenyl unsubstituted or substituted optionally with OH; $NR_5R_6$, or $C_{1-4}$alkoxy; $C_{3-7}$alkynyl unsubstituted or substituted optionally with OH, $NR_5R_6$, or $C_{1-4}$alkoxy; $C_{1-2}$alkyl$C_{1-3}$cycloalkyl or $R_5$ and $R_6$ can be joined to form a ring of 5 or 6 atoms selected from O, S, C or N which can be unsubstituted or substituted optionally on carbon with OH, (=O), halogen, $C_{1-4}$; alkoxy, $C(=O)R_7$, $C_{1-6}$ alkyl, $C_{1-6}$ alkyl substituted optionally with OH, halogen, $C_{1-4}$ alkoxy $C(=O)R_7$ or on nitrogen with $C_{1-4}$ alkoxy, $C(=O)R_7$ $S(=O)_mR_8$, $C_{1-6}$ alkyl or $C_{2-6}$ alkyl substituted optionally with OH, halogen, $C_{1-4}$ alkoxy, $C(=O)R_7$ or on sulfur by $(=O)_m$ wherein m is 0–2;

$R_7$ is $C_{1-8}$ alkyl; $C_{1-8}$ alkyl substituted optionally with OH, $NR_5R_6$, halogen, $C_{1-4}$ alkoxy or $C(=O)R_9$, $C_{1-4}$alkoxy; $C_{2-4}$ alkoxy substituted optionally with OH, $NR_5R_6$, halogen or $C_{1-4}$ alkoxy; or $NR_5R_6$;

$R_8$ is $C_{1-4}$ alkyl; $C_{2-4}$ alkyl substituted optionally with OH, $NR_5R_6$, halogen, $C_{1-4}$ alkoxy or $C(=O)R_7$;

$R_9$ is $C_{1-4}$ alkyl; $C_{1-4}$ alkoxy amino, $C_{1-3}$ alkylamino, or di-$C_{1-3}$ alkylamino; and G is $C(=O)$ or $SO_2$.

24. The method according to claim 19 wherein the carbonic anhydrase inhibitor is selected from a compound of the formula

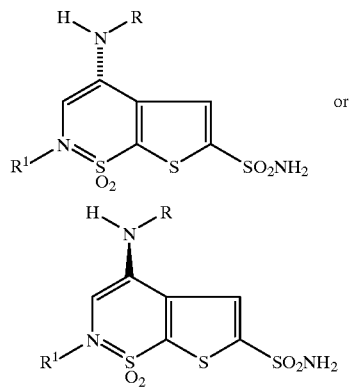

wherein R is selected from —CH₂CH₃ or —CH₂CH₂CH₃ and $R^1$ is selected from $CH_3O(CH_2)_{2-4}$ or a pharmaceutically acceptable salt thereof.

25. The method according to claim 1 wherein the carbonic anhydrase inhibitor is administered as a 0.01 to 5% solution in an ophthalmologically acceptable carrier.

26. The method according to claim 25 wherein the carbonic anhydrase inhibitor is administered as a 0.5 to 2% solution in an ophthalmologically acceptable carrier.

27. The method according to claim 25 wherein the carbonic anhydrase inhibitor is administered twice daily.

28. The method according to claim 25 wherein the carbonic anhydrase inhibitor is administered three times daily.

29. The method according to claim 25, wherein said topical carbonic anhydrase inhibitor is administered as eye drops.

30. A method according to claim 25, wherein said topical carbonic anhydrase inhibitor is administered as a solution, ointment or solid insert topically into said eye.

* * * * *